US011045173B2

(12) United States Patent
Knoll

(10) Patent No.: US 11,045,173 B2
(45) Date of Patent: Jun. 29, 2021

(54) FULL CORE BIOPSY DEVICE

(71) Applicant: PAVE, LLC, Indianapolis, IN (US)

(72) Inventor: Douglas Perianu Knoll, Indianapolis, IN (US)

(73) Assignee: PAVE. LLC, Indianapolis, IN (US)

( * ) Notice: Subject to any disclaimer, the term of this patent is extended or adjusted under 35 U.S.C. 154(b) by 921 days.

(21) Appl. No.: 15/508,926

(22) PCT Filed: Sep. 8, 2015

(86) PCT No.: PCT/US2015/049031
§ 371 (c)(1),
(2) Date: Mar. 5, 2017

(87) PCT Pub. No.: WO2016/037192
PCT Pub. Date: Mar. 10, 2016

(65) Prior Publication Data
US 2018/0153527 A1    Jun. 7, 2018

Related U.S. Application Data

(60) Provisional application No. 62/046,698, filed on Sep. 5, 2014.

(51) Int. Cl.
*A61B 10/02* (2006.01)
(52) U.S. Cl.
CPC ...... *A61B 10/0275* (2013.01); *A61B 10/0233* (2013.01); *A61B 10/0266* (2013.01); *A61B 2010/0208* (2013.01)
(58) Field of Classification Search
CPC ............ A61B 10/0275; A61B 10/0266; A61B 10/0233; A61B 10/02; A61B 10/0283;
(Continued)

(56) References Cited

U.S. PATENT DOCUMENTS

| 4,512,344 A | 4/1985 | Barber |
| 4,907,598 A | 3/1990 | Bauer |

(Continued)

FOREIGN PATENT DOCUMENTS

| CN | 101559002 | 10/2009 |
| JP | SHO64-6915 | 1/1987 |

(Continued)

OTHER PUBLICATIONS

Partial International Search Report corresponding to PCT/US2012/067019, dated Jun. 9, 2015 (6 pages).

(Continued)

*Primary Examiner* — Matthew Kremer
*Assistant Examiner* — Avery M Foley
(74) *Attorney, Agent, or Firm* — Maginot, Moore & Beck, LLP

(57) ABSTRACT

A full core biopsy device includes an outer cannula carried at a proximal end by a outer cannula hub and defining a tissue cutting edge at an opposite distal end, an elongated inner cannula carried at a proximal end by an inner cannula hub and concentrically slidably disposed within the outer cannula. A housing defines a first cavity, a second cavity, and a spring hub between the first and second cavities with a bore in communication between the cavities. An outer cannula spring is disposed within the first cavity between the spring hub and the outer cannula hub. The outer cannula spring is configured to produce a force directed distally against the outer cannula hub. An inner cannula spring is disposed within the second cavity between the spring hub and the inner cannula hub and is configured to produce a force directed proximally against the inner cannula hub. A latch, stop and trigger arrangement is provided to charge the device to compress the two springs and to fire the device to obtain a tissue sample.

9 Claims, 19 Drawing Sheets

(58) Field of Classification Search
CPC ...... A61B 2010/0208; A61B 2010/045; A61B 2010/0283; A61B 2010/0225
See application file for complete search history.

(56) References Cited

U.S. PATENT DOCUMENTS

| | | | |
|---|---|---|---|
| 5,313,958 | A | 5/1994 | Bauer |
| 5,400,798 | A | 3/1995 | Baran |
| 5,490,521 | A | 2/1996 | Davis et al. |
| 5,535,755 | A | 7/1996 | Heske |
| 5,655,542 | A | 8/1997 | Weilandt |
| 5,788,651 | A | 8/1998 | Weilandt |
| 5,916,175 | A | 6/1999 | Bauer |
| 6,015,391 | A | 1/2000 | Rishton et al. |
| 6,083,237 | A | 7/2000 | Huitema et al. |
| 6,126,617 | A | 10/2000 | Weilandt et al. |
| 6,196,978 | B1 | 3/2001 | Weilandt et al. |
| 6,258,045 | B1 | 7/2001 | Ray et al. |
| 6,322,523 | B2 | 11/2001 | Weilandt et al. |
| 6,358,217 | B1* | 3/2002 | Bourassa ........... A61B 10/0275 600/567 |
| 6,494,844 | B1 | 12/2002 | Van Bladel et al. |
| 6,689,072 | B2 | 1/2004 | Kaplan et al. |
| 6,918,881 | B2 | 7/2005 | Miller et al. |
| 7,104,945 | B2 | 9/2006 | Miller |
| 7,137,956 | B2 | 11/2006 | Nishtalas et al. |
| 8,157,746 | B2 | 4/2012 | Eberle et al. |
| 2003/0045873 | A1* | 3/2003 | Hinchliffe ............... A61B 10/04 606/47 |
| 2004/0167428 | A1 | 8/2004 | Quick et al. |
| 2006/0173377 | A1 | 8/2006 | McCullough et al. |
| 2007/0106176 | A1* | 5/2007 | Mark ............... A61B 10/0275 600/566 |
| 2007/0142744 | A1* | 6/2007 | Provencher ........ A61B 10/0266 600/562 |
| 2008/0071193 | A1 | 3/2008 | Reuber et al. |
| 2008/0234602 | A1 | 9/2008 | Oostman et al. |
| 2009/0143808 | A1 | 6/2009 | Houser et al. |
| 2009/0204020 | A1 | 8/2009 | Miller et al. |
| 2009/0275858 | A1 | 11/2009 | Hardin |
| 2010/0317997 | A1 | 12/2010 | Hibner et al. |
| 2011/0152715 | A1 | 6/2011 | Delap et al. |
| 2011/0208089 | A1 | 8/2011 | Sundheimer et al. |
| 2012/0010527 | A1 | 1/2012 | Sundheimer et al. |
| 2013/0023790 | A1* | 1/2013 | Schaeffer ........... A61B 10/0275 600/567 |
| 2013/0053725 | A1* | 2/2013 | Beck ................ A61B 10/0233 600/567 |

FOREIGN PATENT DOCUMENTS

| | | |
|---|---|---|
| JP | HEI8-140980 | 6/1996 |
| JP | 2008528217 | 7/2008 |
| RU | 13534 U1 | 4/2000 |
| SU | 1404068 A1 | 6/1988 |
| WO | 2005013831 A2 | 2/2005 |
| WO | 2008115526 A2 | 9/2008 |
| WO | 2011130216 A1 | 10/2011 |

OTHER PUBLICATIONS

Sales Sheet BioPince Full-Core Biopsy Instruments, Angiotech PBN MEDICALS Denmark A/S Knud Bro Alle 3 KD-3660 Stenlose, date unknown.
W F Dahnert, et al., Fine-needle aspiration biopsy of abdominal lesions: diagnostic yield for different needle tip configurations, Radiology, Oct. 1992, abstract, vol. 185-iss.1, Radiology Society of North America, Inc.
BioPince product description, web page screen print date Nov. 16, 2010, Angiotech Pharmaceuticals, Inc., copyright date 2007-2010.
International Search Report corresponding to PCT/US2012/067019, dated Feb. 28, 2013 (7 pages).

* cited by examiner

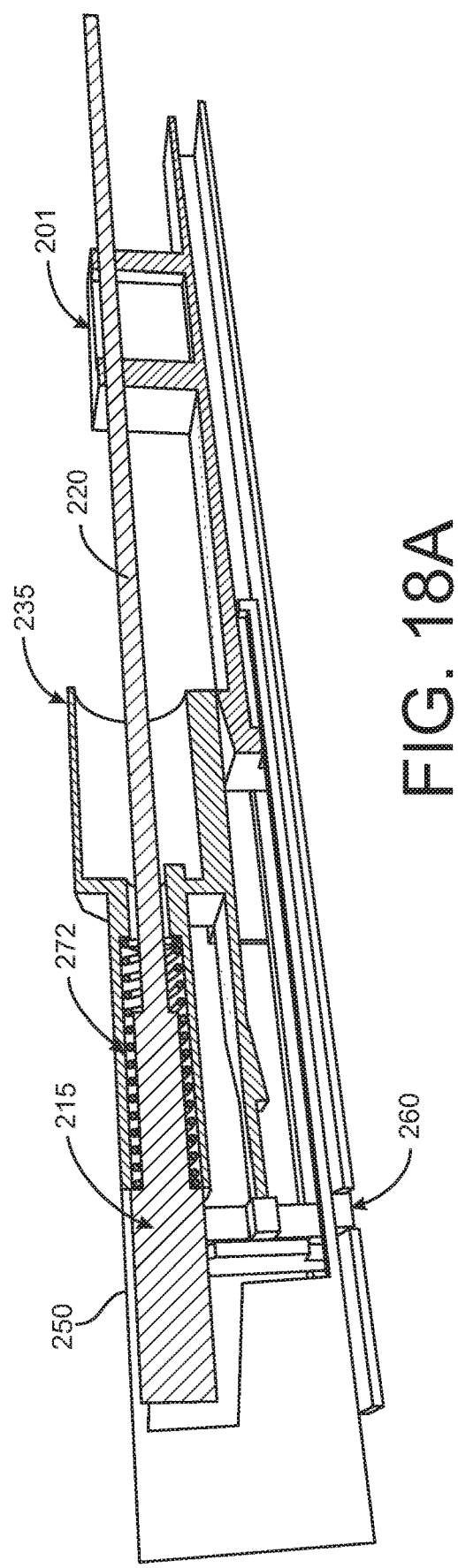

FULL CORE BIOPSY DEVICE

REFERENCE TO RELATED APPLICATION AND PRIORITY CLAIM

This application is a national stage of PCT/US2015/049031, filed on Sep. 8, 2015, which is a utility filing for and claims priority to provisional application No. 62/046,698, filed on Sep. 5, 2014, the entire disclosure of which is incorporated herein by reference.

BACKGROUND

The present invention relates to devices for obtaining a tissue biopsy sample, and more particularly to a device for obtaining a soft tissue core biopsy sample.

Clinicians obtain biopsy specimens for the purpose of diagnosing, staging and grading disease states. One type of biopsy device is a core biopsy needle, which typically operates by coaxial action of an inner needle or stylet having a specimen notch and an outer needle or cannula having a sharp end, with the tip of the inner stylet proud of the end of the outer cannula. The stylet is advanced so that the specimen notch is exposed to tissue, which prolapses into the notch. The cannula is then advanced over the stylet so that the sharp end of the cannula severs the tissue leaving the specimen in trapped within the notch. The volume of the specimen is limited by the notch and the inner diameter of the cannula.

In many biopsy situations, clinicians may desire a full, rounded core sample. The larger cross-section and volume of tissue can provide a more accurate assessment of the tissue pathology. It is also desirable to obtain full, clean core samples that have not been crushed by devices penetrating into tissue, since "crush artifacts" can compromise the analysis of the retrieved sample. In addition, the larger volume of the full core may often provide enough tissue so that only a single pass of the biopsy needle is required. Moreover, it may be desirable to obtain a core sample without having to penetrate past a desired depth of tissue in order to obtain a corresponding desired depth of core sample. It is preferable to insert a biopsy needle only as far as necessary to obtain the desired core sample.

There is a continuing need for biopsy devices, and particularly full core biopsy devices, which can quickly and efficiently obtain large, intact tissue samples. The need is particularly acute for soft tissue samples because the soft tissue can be difficult to extract and retain without damage to the tissue.

SUMMARY

A full core biopsy device comprises an outer cannula hub, an elongated outer cannula carried at a proximal end by the outer cannula hub and defining a tissue cutting edge at an opposite distal end, an inner cannula hub and an elongated inner cannula carried at a proximal end by the inner cannula hub and concentrically slidably disposed within the outer cannula. The device further comprises a housing defining a first cavity, a second cavity, and a spring hub between the first and second cavities and defining a bore in communication between the first cavity and the second cavity. The first cavity is configured to support at least a portion of the inner cannula hub while the bore is configured for passage of the inner cannula therethrough. An outer cannula spring is disposed within the first cavity between the spring hub and the outer cannula hub, the outer cannula spring having a compressed state in which the spring produces a force directed distally against the outer cannula hub. An inner cannula spring is disposed within the second cavity between the spring hub and the inner cannula hub, the inner cannula spring having a compressed state in which the spring produces a force directed proximally against the inner cannula hub.

In a further feature, the biopsy device further comprises a latch arrangement configured to hold the outer cannula hub in a charged position compressing the outer cannula spring within the first cavity and a stop arrangement configured to hold the inner cannula hub in a charged position compressing the inner cannula spring within the second cavity. A trigger is configured to sequentially release the latch arrangement to disengage the outer cannula hub from the charged position to allow the outer cannula spring to drive the outer cannula distally into a tissue site and release the stop arrangement to disengage the inner cannula hub from the charged position to allow the inner cannula spring to drive the inner cannula proximally.

In another aspect, a method is provided for obtaining a full core tissue sample comprising charging a biopsy device having a spring-loaded outer cannula and a spring-loaded concentric inner cannula, introducing the distal end of the outer cannula into a tissue site of a patient, releasing the outer cannula spring to drive the outer cannula into the tissue site to obtain a core tissue sample at the distal end and then releasing the inner cannula spring to drive the inner cannula proximally away from the tissue site.

DESCRIPTION OF THE FIGURES

FIGS. 18a, 18b are perspective partial cross-sectional views of the charging and firing mechanism of FIG. 8 shown as the inner needle is fired by the mechanism.

DETAILED DESCRIPTION

Figure 1:
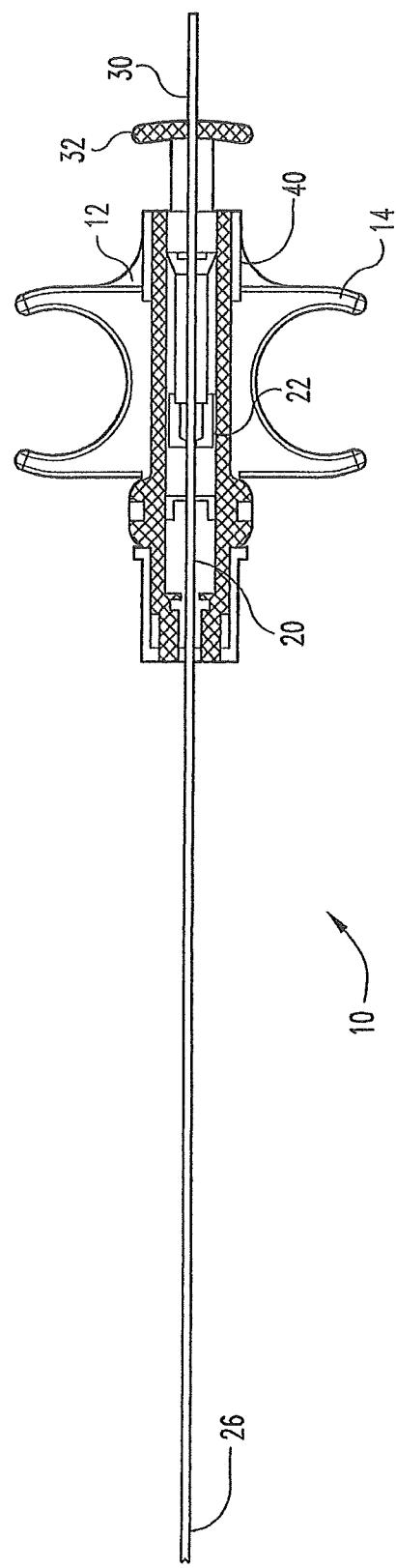
FIG. 1 is a top partial cross-sectional view of a full core biopsy device of the prior art.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

One type of core biopsy device 10 is shown in FIG. 1. The device may include features found in the SABD™ core biopsy system sold by US Biopsy of Franklin, Ind., or similar devices capable of obtaining a core tissue sample from a patient. Although the present disclosure relates to a core biopsy device, the features disclosed herein may be incorporated into other types of tissue sampling or tissue biopsy devices. The device 10 includes a housing 12 that defines finger handles 14 to be grasped by the clinician during a biopsy procedure. The device can include an outer cannula or needle 20 and an inner stylet, cannula or needle 30 coaxially extending through the outer needle 20.

Figure 2:
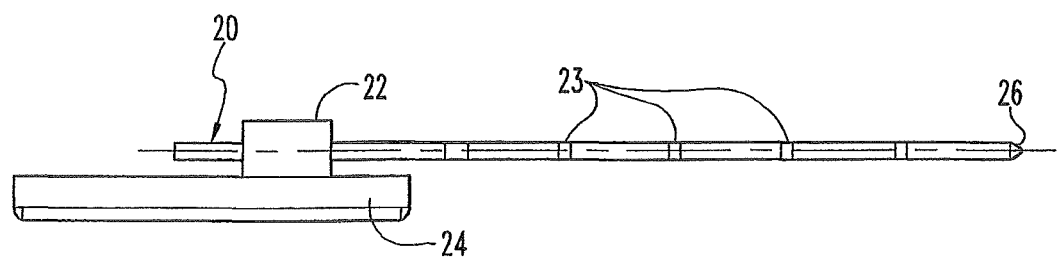
FIG. 2 is a side view of an outer needle component of the full core biopsy device shown in FIG. 1.
Figure 3:
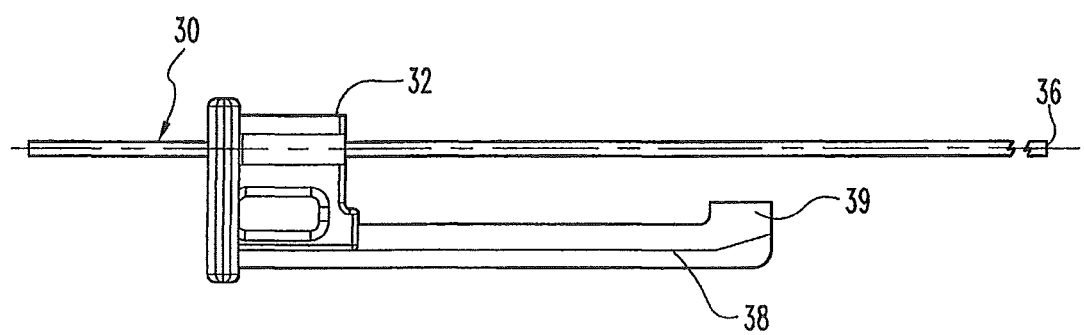
FIG. 3 is a side view of an inner needle component of the full core biopsy device shown in FIG. 1.

The biopsy device 10 incorporates a mechanism for charging and firing the outer needle relative to the inner needle in order to capture a tissue sample. One embodiment of a firing mechanism is described herein although other mechanisms are contemplated that permit charging and firing the outer needle relative to the inner needle to obtain a tissue sample, including semi or fully automated systems. As shown in more detail in FIG. 2, the outer needle 20 is fixed within an outer needle hub 22 mounted on an outer needle carriage 24. Similarly, as shown in FIG. 3, the inner needle 30 is fixed within an inner needle hub 32 mounted on an inner needle carriage 38. The inner needle carriage 38 includes a tab 39 for engaging the outer needle carriage 24 when the biopsy device 10 is charged. The outer needle 20 may include markings 23 used to determine the depth of the outer needle 20 upon insertion into the patient.

Referring back to FIG. 1, the device 10 includes a spring 40 disposed between the housing 12 and the outer needle hub 22. As is known, the device 10 may include a latch (not shown) that holds the outer needle 20 in its charged position. As with many similar biopsy devices, the device 10 is charged by pulling back on the inner needle hub 32, which in turn pulls the outer needle carriage 24 back until it is engaged by the latch. As the outer needle hub 22 is retracted it compresses the spring 40 within the housing 12.

The biopsy device 10 may be fired by pushing the inner needle hub 32 forward so that the tab 39 trips the latch, although other firing mechanisms may be implemented. Once the latch is released the spring 40 propels the outer needle 20 forward over the inner needle and into the subject tissue. In a biopsy procedure, the clinician positions the tip 26 of the outer needle 20 against the tissue to be sampled, with the device in its charged position. When the device is fired, the outer needle 20 advances directly into the tissue so that a core of tissue is captured within the lumen 21 (FIG. 5) of the outer needle 20. The device 10 can be removed from the patient and the tissue core retrieved from the outer needle 20 in a known manner.

As thus far described, the device 10 may be similar in structure and operation to the SABD™ biopsy system and other similar coaxial single action core biopsy devices. The present invention provides improvements to devices of this type and more particularly improvements to the outer and inner needles for use with such devices. However, it is understood that the features described herein may be incorporated into other types of tissue sampling or biopsy devices.

Figure 5:
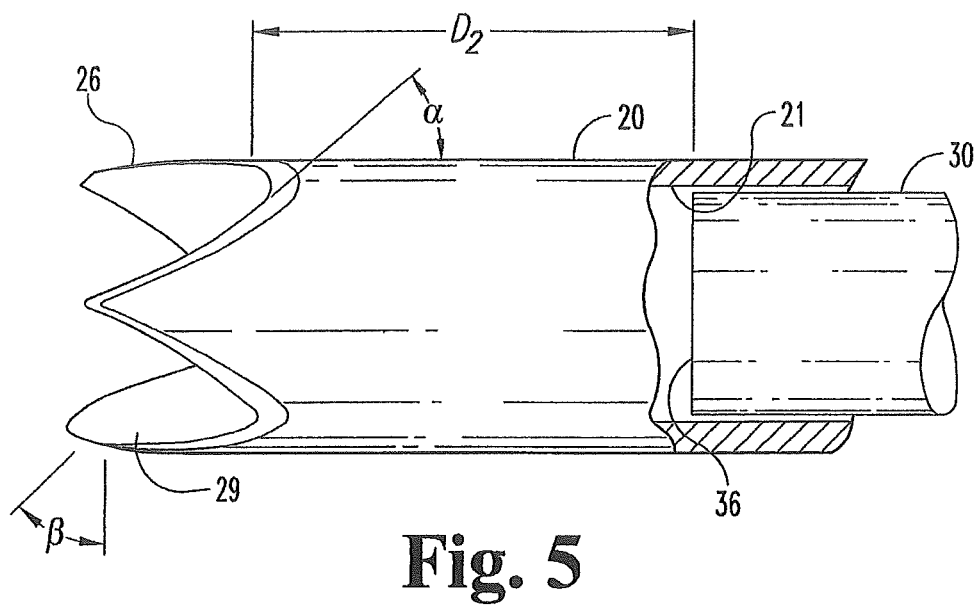
FIG. 5 is an enlarged side view of the end of the outer needle component for use with the full core biopsy device shown in FIG. 1, with the inner needle in its retracted position.
Figure 4:
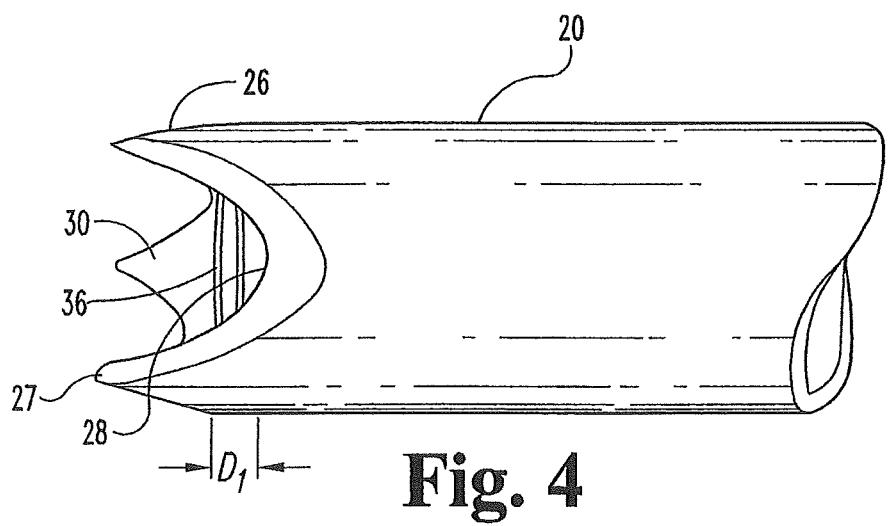
FIG. 4 is an enlarged side view of the end of an outer needle component for use with the full core biopsy device shown in FIG. 1, with the inner needle in its extended position.

According to one aspect, the outer needle 20 is provided with a Franseen tip 26, as shown in FIGS. 4-5. The Franseen tip includes three or more prongs 27 separated by valleys 28 around the circumference of the outer needle tip 26. In one specific embodiment, three prongs 27 are each defined at an angle α, which may be about 18°. The edge surfaces 29 of the prongs 27 may be defined at an angle β, which may be about 30°, to form a sharp cutting edge within the valleys 28. The prongs 27 permits smooth piercing of the soft tissue as the outer needle 20 initially advances into the tissue and solid purchase once the outer needle has been fully advanced. The prongs 27 are configured to advance through the tissue without substantially compressing the tissue. The angled edge surfaces 29 of the prongs 27 act as guillotine cutters to slice cleanly through the tissue as the outer needle 20 advances.

In accordance with one aspect of the disclosed embodiments, the inner needle 30 is maintained in a retracted position relative to the tip 26 of the outer needle 20 when the device 10 is charged as well as when the device 10 is fired. Thus, as shown in FIG. 4, the tip 36 of the inner needle 30 extends only a dimension D1 from the base of the valleys 28 of the tip 26 when the inner needle hub 32 has been moved to trip the latch and release the outer needle 20 as explained above. When the device 10 is initially charged the inner needle tip 36 preferably does not extend beyond, or extends only minimally beyond, the base of the valleys 28 of the tip 26 of the outer needle 20. Put another way, the tip 36 of the inner needle 30 is always offset rearward from the distalmost ends of the prongs 27 of the tip 26 of the outer needle 20, as depicted in FIG. 4. In one embodiment, the dimension D1 is less than about one-fourth of the length of the prongs 27 (i.e., the distance between the base of the valleys 28 and the distal end or top of the prongs 27).

It can be appreciated that in the charged position shown in FIG. 4, the inner needle hub 32 is in position to fire the device 10. Since the device 10 is fired by moving the inner needle hub 32 forward, as explained above, the tip 36 of the inner needle 30 may contact soft tissue if it resides too proud of the outer needle 20. In prior devices the inner stylet extends beyond the end of the outer cutting cannula prior to firing which tends to push the soft tissue away from the cutting cannula, resulting in less than a full core sample or a sample with a crush artifact. In the embodiments disclosed herein, the arrangement of the inner needle 30 relative to the outer needle 20 in the charged and firing positions avoids this condition found in prior devices. It can be appreciated that this positional relationship is produced by appropriate sizing of the length of the outer needle 20 and inner needle 30 taking into account the configuration of the charging and firing mechanism. The inner needle 30 thus has a length that maintains the inner needle tip 36 in the position shown in FIG. 4 when the inner needle hub 32 has been advanced to release the latch holding the outer needle hub 22 against the compressed firing spring 40.

In yet another approach, the inner needle 30 can be mounted within the inner needle hub 32 to permit deliberate retraction of the inner needle 30 prior to firing to ensure that the inner needle tip 36 is clear of the outer needle tip 26. Thus, a threaded arrangement may be incorporated between the inner needle 30 and the inner needle hub 32 configured so that rotation of the inner needle 30 backs the needle out from the inner needle hub 32. As the inner needle 30 backs out relative to the inner needle hub 32, the inner needle tip 36 is retracted from the outer needle tip 26. The threaded engagement may be configured to prevent complete disengagement of the inner needle 30 from the inner needle hub 32 and may preferably incorporate a locking mechanism to lock the inner needle 30 in its retracted position when the biopsy device 10 is fired. With this embodiment, once the biopsy device 10 is charged the clinician takes the additional step of rotating the inner needle 30 to retract the tip 36 prior to firing the device. The inner needle 30 may be provided with a finger tab at its proximal end to facilitate manual rotation of the needle.

As shown in FIG. 5, after the device 10 is fired, the inner needle 30 is offset rearward from the tip 26 of the outer needle 20 by a dimension D2 because the outer needle 20 has been driven forward by the firing spring 40. This dimension is calibrated to the length of the tissue core desired and is generally based on the throw of the device 10 achieved by the charging and firing mechanism—i.e., the distance that the outer needle 20 travels when propelled by the spring 40. In certain full core biopsy devices the throw of the outer needle may be fixed, while in other such devices the throw may be adjustable to vary the length of the tissue sample that is obtained.

After the device has been fired, the excised tissue sample is retained within the end of the outer needle 20. The inner needle 30 may then be used to expel the tissue sample. This can be accomplished by charging the device—i.e., by pulling back on the inner needle hub 32—which withdraws the outer needle 20 to its initial charged position. With the outer needle 20 charged, the inner needle 30 can be freely advanced forward far enough to push the tissue sample out of the outer needle 20, but not so far as to release the latch and dry fire the device 10. The inner needle 30 would thus be advanced to the position shown in FIG. 4. Since the inner needle 30 is used to expel the sample, it is desirable that the tip 36 of the inner needle 30 be immediately proximate the base of the valleys 28 of the tip 26 of the outer needle 20. This position of the inner needle tip 36 will ensure that the soft tissue sample is dislodged from the outer needle 20 either freely or with only minor urging so as not to destroy the sample.

In certain uses of the device 10 the preferred initial step may be to insert an introducer and stylet to the biopsy site. The stylet is removed and the device 10 is charged and passed through the introducer until the outer needle tip 26 is initially engaged with the soft tissue. The device 10 is then fired and removed through the introducer. To remove the biopsy sample, the device 10 is charged again and the inner needle 30 is slowly advanced forward as the device 10 itself is moved backward over the receiving surface (similar to putting icing on a cake). Once the inner needle 30 reaches the end of its stroke, the biopsy sample should be fully and cleanly dislodged from the outer needle 20.

It can be appreciated that the action of the inner needle 30 is an important factor in producing an intact full-core biopsy sample. The inner needle tip 36 may be closed so that tissue cannot migrate into the inner needle 30. The inner needle tip 36 may be slightly concave to urge the trailing tissue toward the center of the inner needle 30. The inner needle 30 is sized for a close running fit within the inner lumen 21 of the outer needle 20 (FIG. 5), and to prevent passage of tissue into the gap between the inner needle 30 and outer needle 20.

It can be appreciated that the combination of the Franseen tip 26 and the relative positioning between the inner needle 30 and outer needle 20 described above provides a significantly greater chance of obtaining a full, clean core biopsy sample that has not been crushed without having to penetrate past a desired depth of tissue in order to obtain a corresponding desired depth of core sample. The Franseen tip 26 of the device 10 provides a cleaner cut with only linear motion and without rotation of the outer needle 20. This helps reduce the chance of crushing the sample. The relative position of the inner needle 30 and the outer needle 20 also reduces the chance of crushing the sample and helps reduce the depth in the tissue that the device 10 must travel to obtain its full, clean core biopsy sample.

Figure 6:
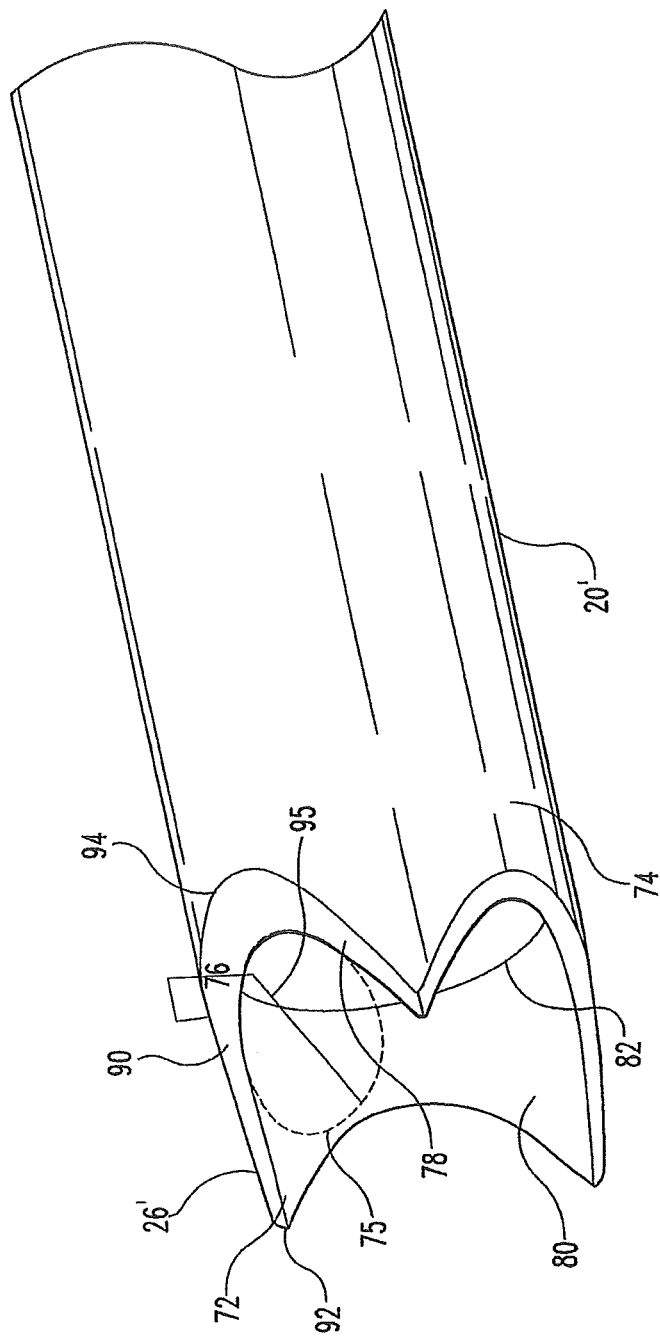
FIG. 6 is an enlarged view of an outer needle component for use with the full core biopsy core device of FIG. 1.

In another embodiment, shown in FIG. 6, an outer needle 20' includes an inner surface 72 and an outer surface 74. The outer needle 20' defines a thickness 76 between the inner surface 72 and the outer surface 74. In one aspect, the inner surface of the outer needle includes features for enhancing retention of the tissue within the outer needle once the device has been fired. Thus, in one embodiment, this retention feature includes a countersink or forcing cone 80 defined in the inner surface 72. The forcing cone further leads to a sharper cutting edge 78 at the tip of the outer needle.

Figure 7:
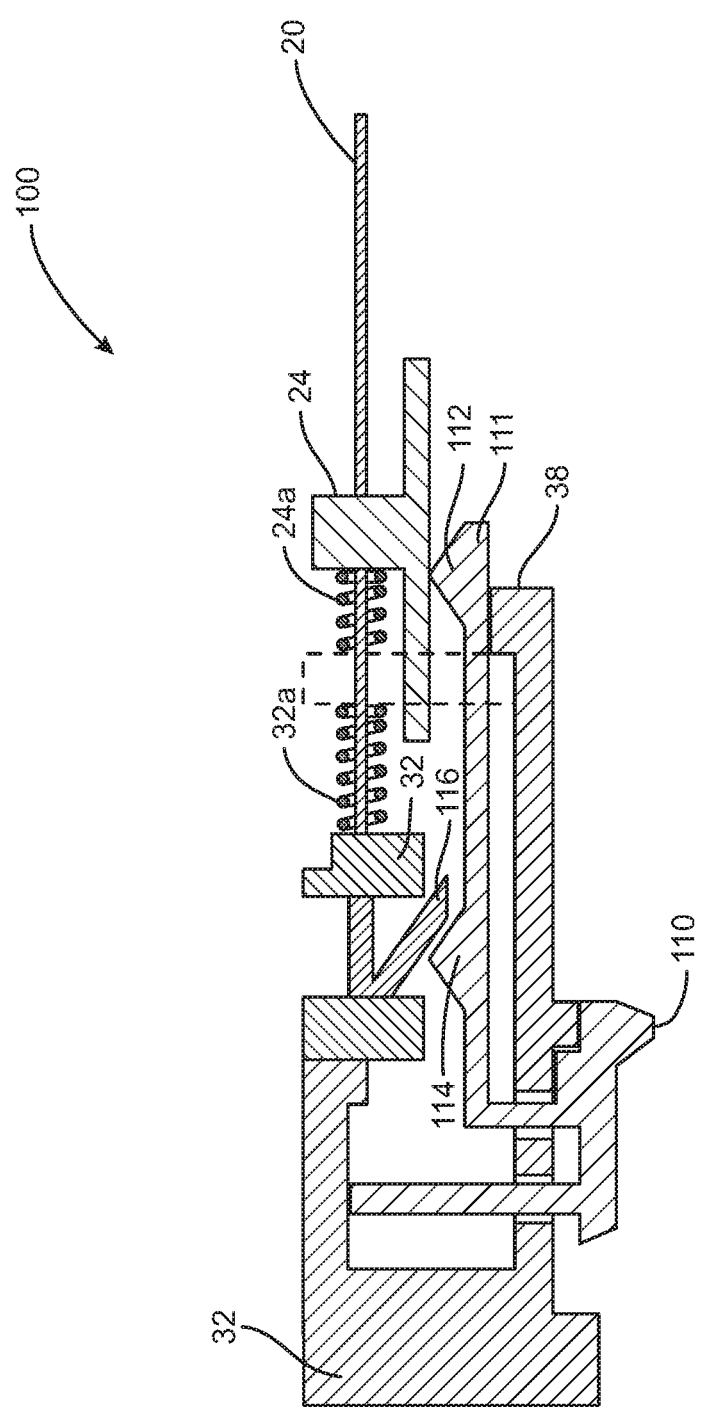
FIG. 7 is a schematic diagram of a charging and firing mechanism for the full core biopsy device of FIG. 1 according to one aspect of the present disclosure.

The countersink or forcing cone 80 is formed in the inner surface 72 of the outer needle 20' and extends from the tip to an inner end 82. The inner end 82 is located at a depth D3 that may be, in certain embodiments, approximately twice the diameter 95 defined by the valley 75 between the prongs 92 the tip 26'. The forcing cone 80 is formed such that the thickness 76 of the outer needle 20' is greater at the inner end 82 than at the tip 26'. In other words, the thickness at the inner end 82 is equal to the wall thickness of the tubular body of the outer needle 20' but tapers to a sharp cutting edge 78 at the tip 26'. The forcing cone 80 is formed in the inner surface 72 at an angle γ as shown in FIG. 7. In certain embodiments, the angle γ may be about 3-4° so that the countersink or forcing cone 80 forms an included angle of about 6-8°.

The forcing cone 80 assists in retaining the tissue within the outer needle when the device is fired and when the excised tissue is being removed. It is believed that the forcing cone tends to compress a greater volume of tissue into the outer cannula during the coring operation and that this greater volume in turn provides additional surface tension or pressure between the tissue sample and the forcing cone 80. This increased pressure allows the tissue sample to "grip" the inner surface of the outer needle as the device is being extracted from the tissue site.

The cutting edge 78 is formed by the intersection of the forcing cone 80 with the outer surface 74. Because the countersink or forcing cone 80 decreases the thickness 76 of the outer needle 20', it produces a much sharper cutting edge 78. The thickness of the cutting edge 78 may be approximately 0.0005 to 0.001 inches.

In another aspect, the outer needle 20' may further include a tissue slicing feature 90 formed in the outer surface 74. The tissue slicing feature 90 also reduces the thickness 76 of the outer needle 20' so that the tip 26' is the thinnest portion of the outer needle 20'. The tissue slicing feature 90 may be, for example, a Franseen tip (as described above with reference to FIGS. 4-5 and as shown in FIG. 6). Other suitable slicing configurations may be a Trocar tip, a Quinke tip or any other needle point feature that forms a sharp tip and edge.

In this embodiment, the thickness 76 of the outer needle 20' varies along its length due to the introduction of the described features. The thickness 76 of the outer needle 20' between the hub 22 and the inner end 82 of the forcing cone 80 may be approximately 0.003 or 0.004 inches. The thickness 76 of the outer needle 20' begins to decrease by the angle γ at the inner end 82 of the forcing cone 80 and begins to decrease further by the angle α at the valleys 94 of the tissue slicing feature 90. The thickness 76 at the tip 26' may be thus reduced to approximately 0.0012 to 0.0014 inches.

The result of the embodiment described above, including both the countersink or forcing cone 80 and the tissue slicing feature 90, is a complete and uniform core sample trapped within the end of the outer needle 20', without any crush artifact. The tissue slicing feature 90 of the device 20' provides a cleaner cut with only linear motion and without rotation of the outer needle 20'. Furthermore, the countersink or forcing cone 80 of the device 20' provides a guiding surface to guide and support the core as it is cut away from the tissue by the cutting edge 78 of the outer needle 20'.

The outer needle 20' may include other tissue retention features formed in the inner surface 72 of the outer needle in conjunction with or in lieu of the forcing cone 80. Thus, in one feature a spiral groove 85 is formed in the inner surface 72. The groove 85 may be formed in the inner surface 72 at a location adjacent the inner end 82 of the forcing cone 80, as shown in FIG. 7. In this embodiment, the groove 85 has a depth of 0.04 to 0.08 inches. The groove 85 is shown as commencing at the end 82 of the forcing cone, although in other embodiments the groove may overlap the forcing cone. It is believed that the groove enhances the "grip" between the outer needle and the tissue being excised, particularly when combined with the forcing cone 80. It is contemplated that other tissue retention features may be incorporated into the inner surface 72 of the outer cannula. For instance, rather than a spiral groove, such as the groove 85, the feature may include a series of circumferential grooves, axial grooves, striations, ridges, knurling or other features that provide an irregular surface into which the tissue may swell. However, the spiral groove may be preferred for manufacturing reasons.

In one embodiment, the outer needle 20 of the full core biopsy device 10 may include a countersink or forcing cone 80 along with a predetermined relative positioning between the inner needle 30 and the outer needle 20'. In this embodiment, the inner needle 30 can have a length that maintains the inner needle tip 36 in a position (not shown) such that the inner needle tip 36 is situated in the outer needle 20' between the hub 22 and the inner end 82 of the countersink or forcing cone 80. In other words, the tip of the inner needle may be offset proximal or inboard of the inner end 82 of the forcing cone 80. This embodiment combines the advantages provided by the relative positioning of the inner and outer needles (in the same manner as described above in reference to the inner needle 30 and outer needle 20 of FIGS. 4-5) with the advantages provided by the forcing cone 80 as described above. Likewise, the other retention features, such as the spiral groove 85, may be incorporated into the full core biopsy device 20. In a further alternative, the inner and outer needle, as well as the charging and firing mechanism, can be configured so that the inner needle distal tip is "proud" of the outer needle distal tip, meaning that the inner needle tip 36 extends beyond the outer needle tip 26 prior to firing the device.

In a modification of the biopsy device 10, a mechanism 100 shown in FIG. 7 is introduced that simplifies the charging and firing of the device and that causes the inner needle or stylet to retract after the outer needle or cannula has advanced into the tissue. The mechanism 100 includes a slide trigger 110 that is accessible on the housing 12 of the device. The slide trigger is used to fire the device rather than the plunger 32 as in the prior embodiment. The plunger 32 is still used to charge the device. In particular, retracting the plunger 32 charges the outer cannula 20 by retracting the outer cannula hub 24 against its activation spring 24a. The slide trigger 110 is configured to be retracted as well when the plunger is retracted.

The plunger is then advanced forward to push the inner stylet hub 32 forward against the inner stylet spring 32a to charge the inner stylet. The forward movement of the plunger does not move either the outer cannula hub or the slide trigger. The device is then ready to be introduced into the target tissue. With the distal working end of the device positioned within the tissue, the slide trigger 110 is moved forward to fire the device. As the slide trigger moves forward, a cam surface 112 on an arm 111 of the slide trigger releases the outer cannula hub 24 so that the spring 24a propels the outer cannula 20 forward into the tissue, as with the device described above.

The arm 111 of the slide trigger 110 is also provided with a second cam surface 114 that is offset proximally from the first cam surface. The second cam surface is spaced from a release lever 116 that releases the inner cannula hub 32. In particular, the second cam surface is spaced farther from the release lever 116 than the first cam surface 112 is spaced from the outer cannula hub release. Consequently, there is a time delay from when the first cam surface 112 releases the outer cannula hub 24 and outer cannula 20 and the second cam surface 114 releases the inner cannula hub 32. When the inner cannula hub is released, the spring 32a propels the inner cannula backward—i.e., in the opposite direction to the outer cannula firing direction. This retrograde movement of the inner needle/cannula/stylet helps draw the tissue deeper into the full core outer cannula and applies a slight negative pressure to hold the tissue sample within the outer cannula 20.

With the tissue sample trapped within the outer cannula 20, the device can be removed from the patient. The full core tissue sample can be retrieved by pulling the plunger 32 back, which brings the outer cannula, inner stylet and slide trigger back at the same time. Moving the inner stylet back with the outer needle keeps the distal tip of the stylet clear of the full core tissue sample lodged within the outer cannula, thereby avoiding unintended discharge of the sample. Once the device is positioned within a tissue staging area, the plunger 32 can be pushed forward again to expel the tissue sample from the outer cannula. Since the slide trigger is not connected to the plunger at this point, there is no risk of accidental firing of the device.

A charging and firing device 200 according to another embodiment is shown in FIGS. 8-14. The device 200 provides similar benefits to the device 100 shown in FIG. 7, namely providing a simplified process for charging and firing the outer and inner cannulae, providing retrograde movement of the inner cannula/stylet to help draw tissue into the outer cannula/needle, and a providing the ability to easily discharge a tissue sample from the outer cannula/needle. The mechanism 200 includes an outer cannula element 201, shown in detail in FIG. 9, having a hub 202 within which the outer cannula or needle 204 is mounted in a manner similar to the outer cannula 20 described above. The outer cannula 204 is preferably configured as the full core cannula shown in FIGS. 5, 6. The hub 202 is integral with a track 206 that is used to guide the linear movement of the outer cannula element 201. The track includes a rear portion 207 that is directed proximally (i.e., to the left as viewed in FIG. 8). The proximal end 208 of the portion 207 includes a ramp 210 that defines a ramp face 211. The opposite side of the track 206 is formed as a latch 213 at the proximal end 208. It is noted that the ramp 210 as well as other ramps disclosed herein are provided to facilitate displacement of mating components, as described in more detail herein.

Figure 8:
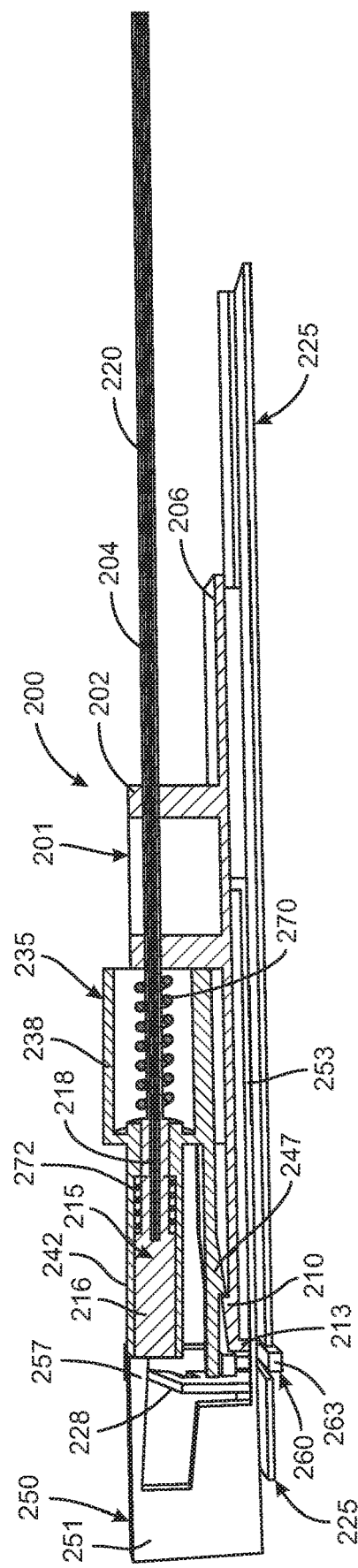
FIG. 8 is a side cross-sectional view of a charging and firing mechanism for use with the full core biopsy device of FIG. 1 according to a further aspect of the present disclosure.
Figure 9:
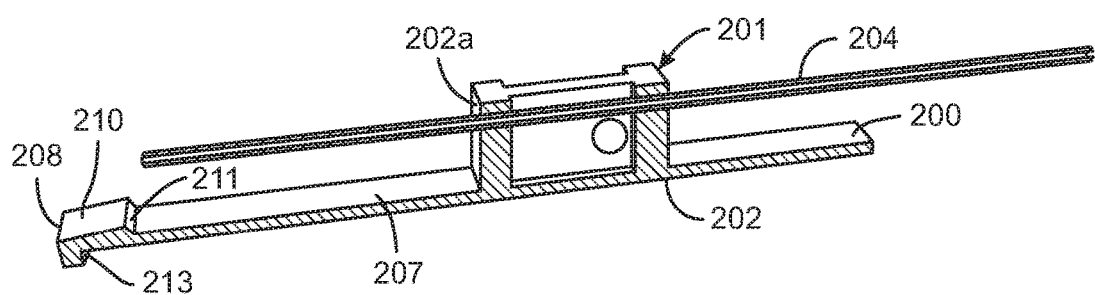
FIG. 9 is a perspective cross-sectional view of an outer needle element of the charging and firing mechanism of FIG. 8.
Figure 10:
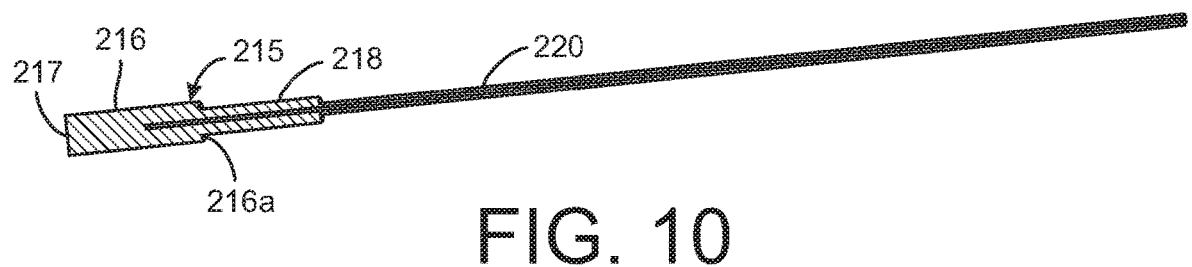
FIG. 10 is a perspective cross-sectional view of an inner needle element of the charging and firing mechanism of FIG. 8.

The device further includes an inner cannula element 215 that includes a hub 216 with a distal end 217 and a spring guide 218 extending from the distal end. The inner cannula element 215 includes an inner cannula, stylet or needle 220 that is embedded within the hub 216 in a conventional manner. The inner cannula 220 may be configured similar to the cannula 36 described above. The inner cannula 220 is concentrically disposed within the outer cannula 204, as depicted in FIG. 8.

Figure 11:
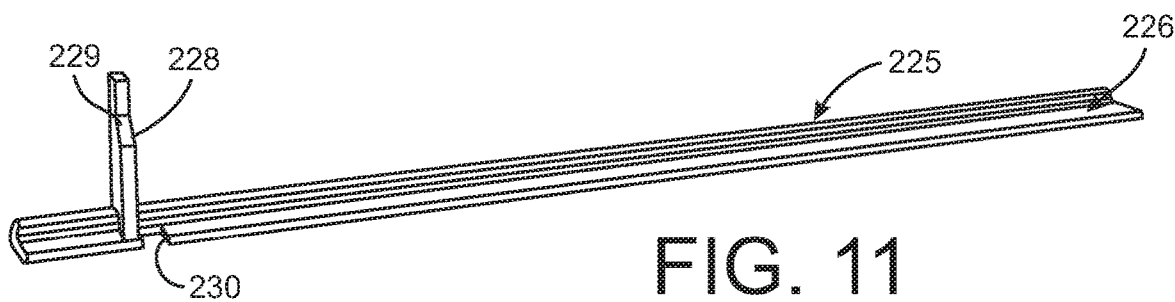
FIG. 11 is a perspective cross-sectional view of a tracking guide of the charging and firing mechanism of FIG. 8.

The mechanism 200 further includes an elongated tracking guide 225 shown in FIG. 11 that provides a guide channel 226 along which the outer cannula hub 202 and track 206 travel during charging and firing of the mechanism. The tracking guide 225 includes a plunger stop 228 adjacent the proximal end of the guide. The plunger stop includes an upper edge forming a trigger support 229. The base of the tracking guide 225 further defines a trigger notch 230 immediately adjacent the plunger stop 228. It can be appreciated that the tracking guide is fixed within a housing for a biopsy device that incorporates the mechanism 200.

Figure 12:
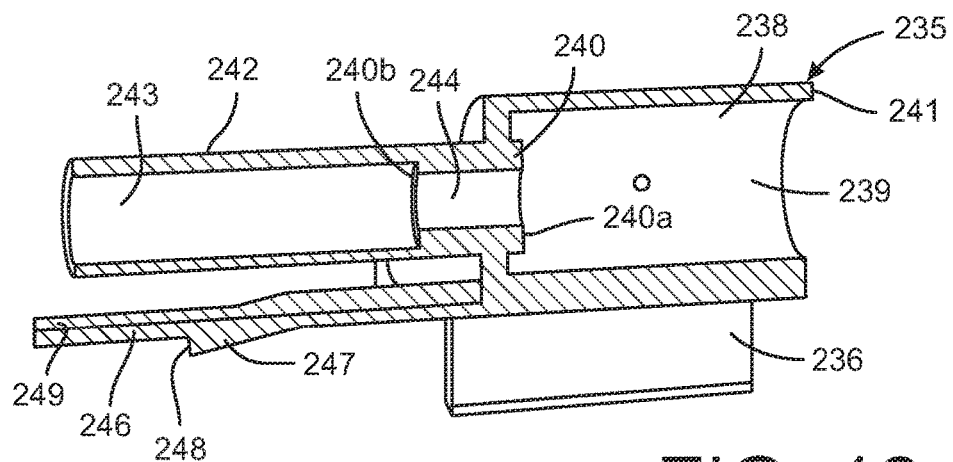
FIG. 12 is a perspective cross-sectional view of a spring housing of the charging and firing mechanism of FIG. 8.

The mechanism 200 further includes a spring housing 235, shown in FIG. 12, which is also fixed within the device housing by way of a mounting plate 236. The spring housing 235 includes an outer cannula spring casing 238 that defines a first cavity 239 through which the inner cannula 220 extends. A spring housing defines a spring hub 240 inside the cavity which supports a first outer cannula spring 270 (FIG. 8). As shown in FIG. 8, the first spring 270 is disposed within the first cavity 239 between proximal face 202a the outer cannula hub 202 and the distal face 240a of the spring hub 240. The distal face 241 of the outer spring casing 238 provides a proximal stop surface for the outer cannula hub 202 for movement of the hub in the proximal direction (to the left in FIG. 8).

The spring housing 235 further includes an inner cannula spring casing 242 that is integral with the outer cannula spring casing 238. The inner cannula spring casing 242 defines a second cavity 243 and a cannula bore 244 connecting the second cavity 243 to the first cavity 239. The cannula bore 244 is sized to receive the inner cannula 220 and spring guide 218 of the inner cannula element 215 therethrough, while second cavity 243 is sized to receive the inner needle hub 216. A second inner cannula spring 272 (FIG. 8) is disposed within the second cavity 243 around the inner cannula element 215. In particular, the second spring 272 is disposed between the proximal face 240b of the spring hub 240 and the distal face 216a of the inner cannula hub 216.

The first spring 270 is compressed within the first cavity 239 of the outer cannula spring casing 238 in the charged configuration depicted in FIG. 8. When the spring 270 is discharged it propels the outer cannula element 201 distally, i.e., to the right in FIG. 8. The inner cannula spring 272 is compressed within the second cavity 243 of its corresponding spring casing 242. When the second spring 272 is discharged, it propels the inner cannula element 215 proximally, i.e., to the left in FIG. 8.

Figure 13:
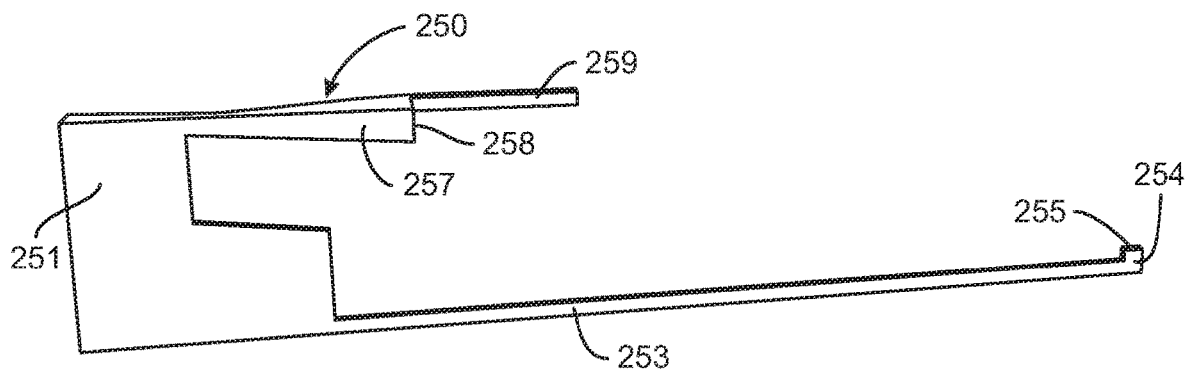
FIG. 13 is a perspective cross-sectional view of a plunger of the charging and firing mechanism of FIG. 8.

The mechanism 200 further includes a plunger 250 shown in FIG. 13 that is used to charge the biopsy device. The plunger 250 includes a plunger grip 251 that is manually accessed to slide the plunger. A latch arm 253 extends from the plunger grip within the guide channel 226 (FIG. 8). The distal end 254 of the latch arm 253 includes an engagement tab 255 that is configured to engage the latch 213 of the outer cannula element 201. The plunger further includes an upper arm 257 that provides an inner cannula stop 258 that is aligned with the proximal face 216a of the inner cannula hub 216. A guide arm 259 may be provided that helps guide and control the translation of the plunger 250.

Figure 14:
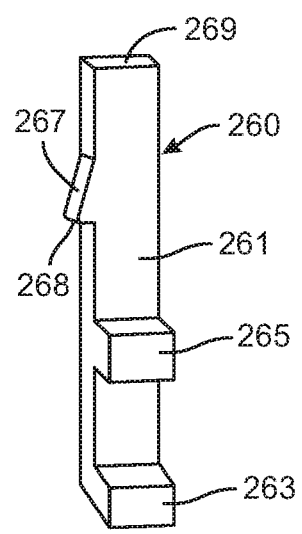
FIG. 14 is a perspective cross-sectional view of a trigger of the charging and firing mechanism of FIG. 8.

The mechanism 200 is provided with a trigger 260 shown in FIG. 14 that is operable to fire or discharge the biopsy device. The trigger 260 includes an elongated beam 261 that extends through the trigger notch 230 in the tracking guide 225. The beam 261 includes an actuation end 263 that projects below the tracking guide 225 in its neutral position. The actuation end 263 is configured to receive manual pressure to push the trigger 260 upward relative to the tracking guide. The beam 261 further includes a release flange 265 that is about a third up the length of the beam. The release flange 265 is arranged to be positioned directly beneath the flex arm 246 of the spring housing 235. A stop flange 267 is provided further up the beam 261 and it arranged so that a stop surface 268 contacts the plunger stop 228 of the tracking guide to retain the trigger within the device housing. The beam 261 defines a release end 269 at the top of the beam that is arranged directly beneath the upper arm 257 of the plunger in the charged configuration shown in FIG. 8. It is noted that the trigger beam 262 positioned outboard of the inner cannula element 215 so that it does not interfere with proximal movement of the element during operation of the mechanism 200. Alternatively, the release end 269 can be arranged inboard of the trigger beam 262 and configured with a ramp surface to push the trigger beam laterally outward away from the inner cannula element.

Figure 15A:
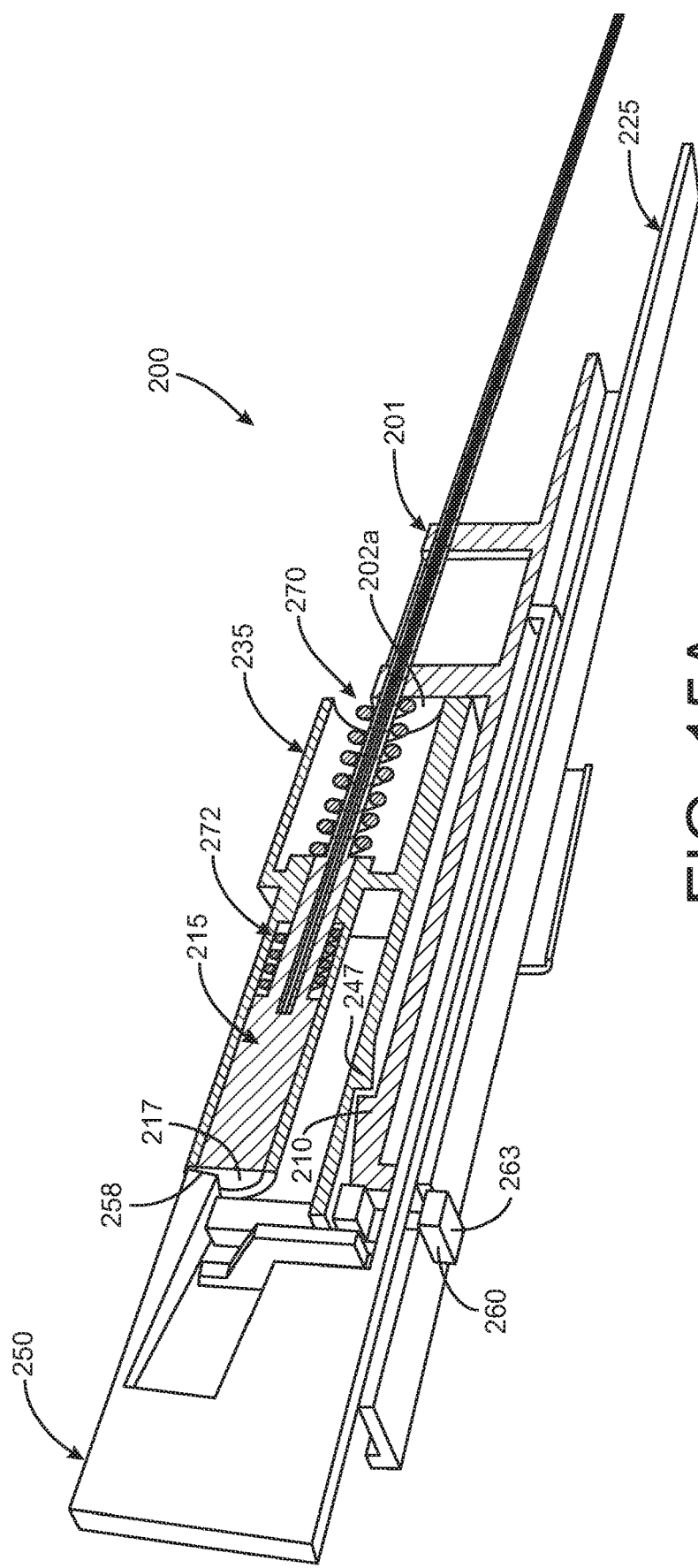
FIGS. 15a, 15b are perspective partial cross-sectional views of the charging and firing mechanism of FIG. 8 shown in its charged configuration.
Figure 15B:
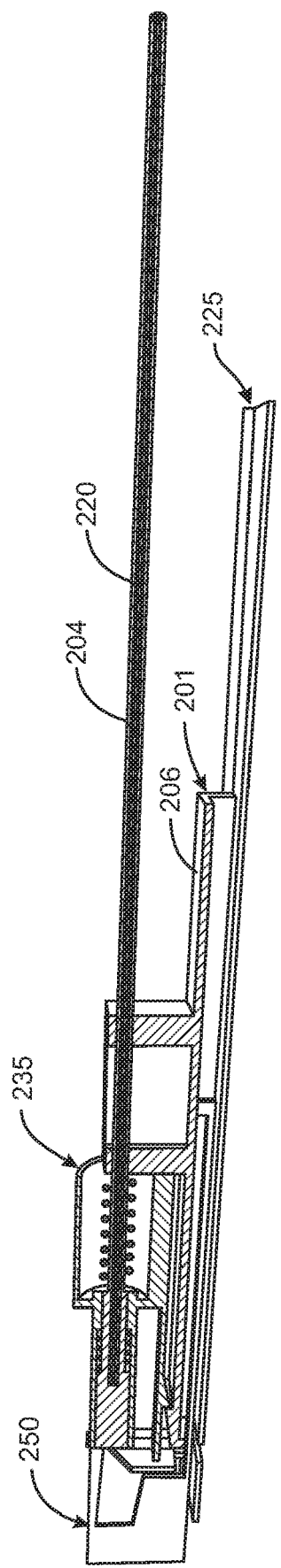

The charging and firing mechanism 200 is shown in its charged condition in FIGS. 15a, 15b. In this position, both springs 270, 272 are fully compressed within their respective casings 238, 242. The outer cannula element 201 is held by the engagement between ramp face 211 of the charging ramp 210 and the stop face 248 of the ramp 247 of the spring housing 235. The inner cannula element 215 is held by the engagement between stop 258 of the plunger 250 and the proximal face 217 of the inner cannula hub 216. In this charged position, the inner and outer cannula can have the positions shown in FIG. 5 with the distal tip of the inner cannula slightly proximal of the distal tip of the outer cannula. However, it is understood that the lengths of the inner and outer cannulae can be adjusted to achieve other relative positions of the distal tips. The biopsy device incorporating the mechanism 200 is maneuvered to the biopsy site so that the distal tips of the cannulae are positioned to obtain a core biopsy specimen at the site. This step can be accomplished in a known manner.

Figure 16:
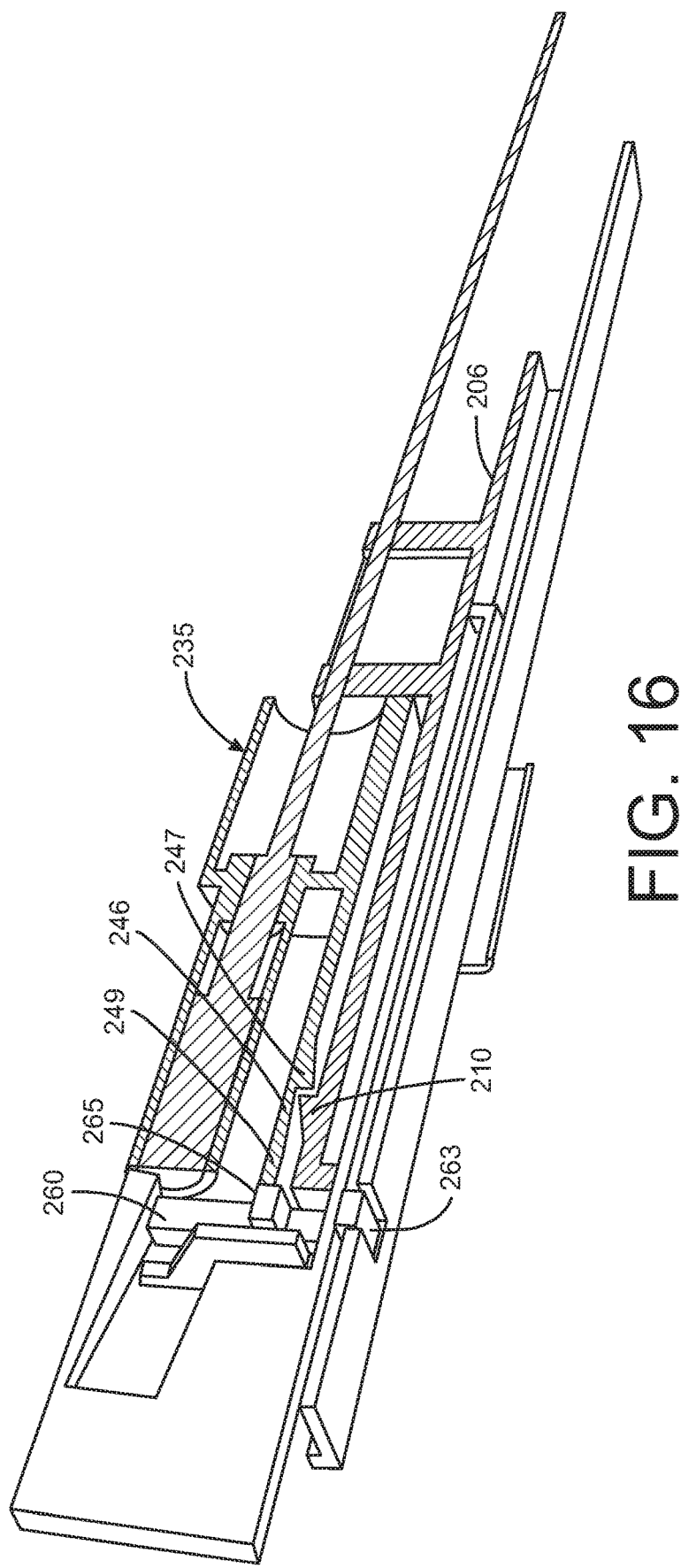
FIG. 16 is a perspective partial cross-sectional view of the charging and firing mechanism of FIG. 8 shown with the trigger actuated.
Figure 17A:
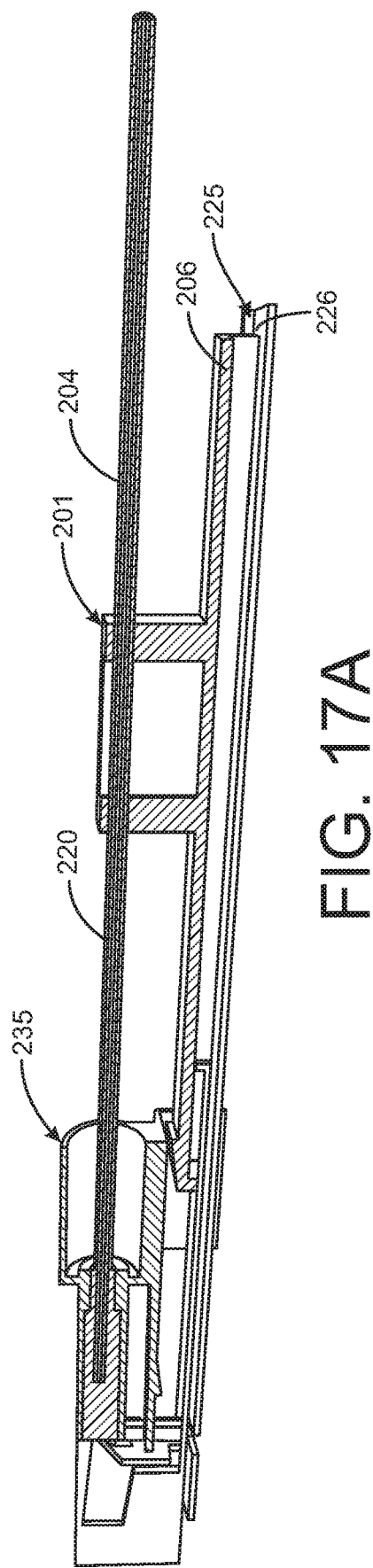
FIGS. 17a, 17b are perspective partial cross-sectional views of the charging and firing mechanism of FIG. 8 shown as the outer needle is fired by the mechanism.
Figure 17B:
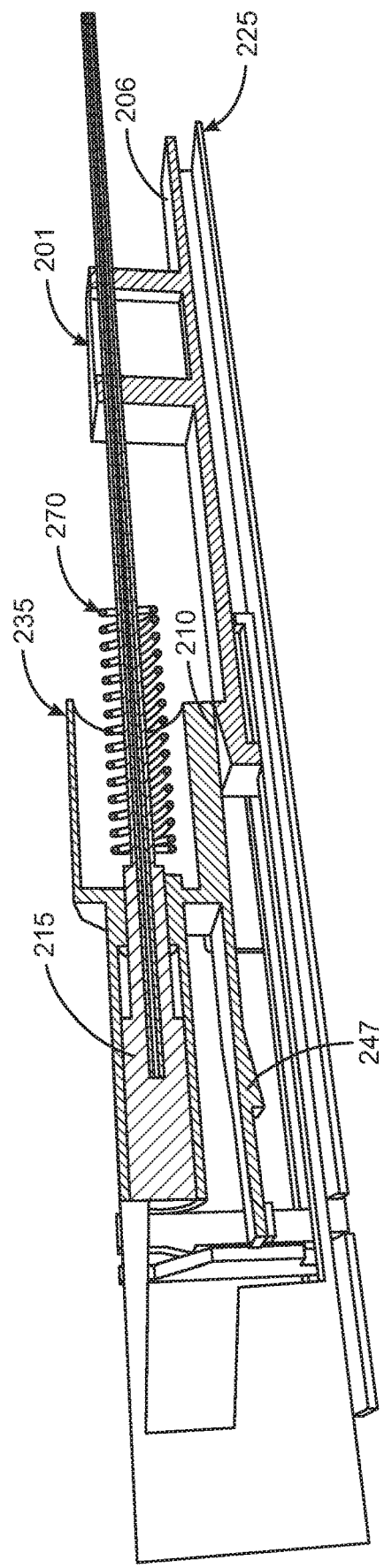

With the distal tip of the outer cannula properly positioned, the mechanism can be fired or discharged so that the outer cannula 204 advances into the tissue to obtain the full core specimen. This is accomplished by depressing the actuation end 263 of the trigger 260 from the extended position shown in FIG. 15*a* to the depressed position shown in FIG. 16. As the trigger 260 is depressed, the release flange 265 contacts the proximal end 249 of the flex arm 246 of the spring housing 235. The upward movement of the trigger thus pushes the flex arm 246 upward so that the ramp 247 disengages from the ramp 210 at the rear portion 207 of the outer cannula track 206. Once the track 206 of the outer cannula element 201 is disengaged from its stop, the first spring 270 propels the outer cannula hub 202 and outer cannula 204 distally to the position shown in FIG. 17*a* (in which the spring has been omitted for clarity) and FIG. 17*b*. The track 206 travels along the guide channel 226 of the tracking guide 225 so that the outer cannula 204 travels smoothly along the desired path to obtain the core tissue sample. It is contemplated that the outer cannula track 206 and the guide channel 226 can incorporate features to ensure that the outer cannula does not deviate from the tracking guide as it is propelled distally by the force of the spring 270. It is understood that the inner cannula remains in its charged configuration at least initially while the biopsy sample is obtained by the outer cannula 204.

Figure 18B:
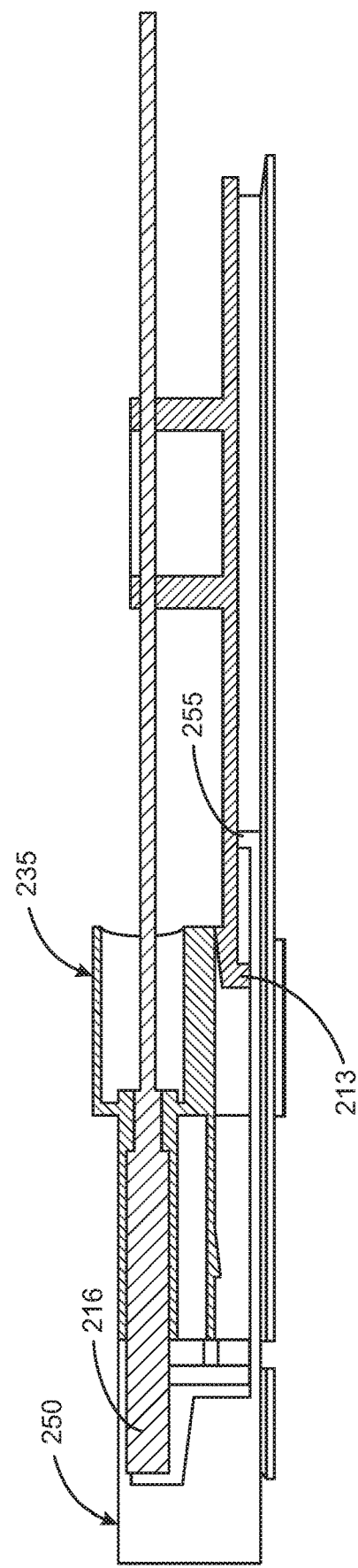

However, the inner cannula does not remain inert during the movement of the outer cannula. As the trigger 260 is moved further upward, the release end 269 contacts the upper arm 257 of the plunger and moves the arm upward. This movement disengages the inner cannula stop 258 from the proximal face 216*a* of the inner cannula hub 216 thereby releasing the inner cannula element 215. Once released, the second spring 272 discharges to propel the inner cannula element 215 proximally, i.e., to the left as shown in FIGS. 18*a*, 18*b*. With this movement, the inner cannula 220 is retracted within the outer cannula 204 relative to the biopsy site. This retraction facilitates the passage of the tissue into the outer cannula 204, optimally providing a longer tissue core.

Figure 19A:
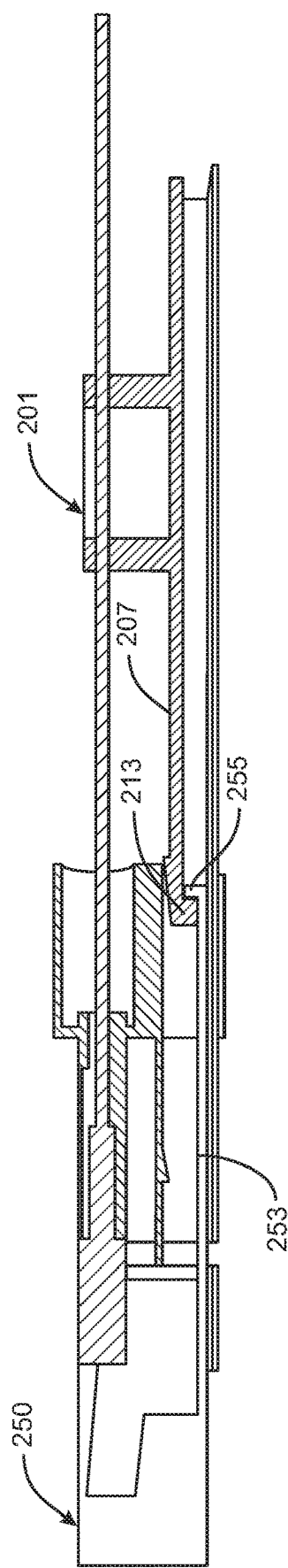
FIGS. 19a, 19b are perspective partial cross-sectional views of the charging and firing mechanism of FIG. 8 shown as the plunger is retracted.
Figure 19B:
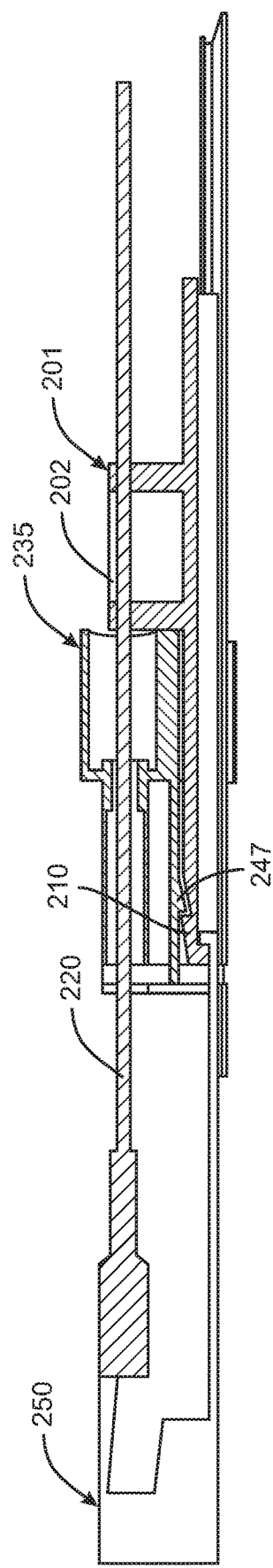

The distal movement of the outer cannula 204 and the proximal movement of the inner cannula 215 occur very rapidly so that the tissue is forced into the body of the outer cannula. The combination of the movements of the cannulae essentially engorges the outer cannula with the tissue sample so that the friction and pressure between the tissue and the outer cannula holds the tissue core embedded within the outer cannula. The tissue sample can be separated from the tissue site by pulling the outer cannula proximally away from the tissue site. Thus as shown in FIGS. 19*a*, 19*b*, the plunger is retracted proximally away from the tissue site. It can first be noted that when the outer cannula is fired its ending position as shown in FIGS. 18*a*, 18*b* positions the latch 213 distally away from the engagement tab 255 of the plunger 250. When the plunger 250 is retracted as shown in FIG. 19*a* the engagement tab 255 at the end of the latch arm 253 is pulled proximally until it engages the latch 213 of the outer cannula element 201. Continued movement of the plunger continues until the outer cannula hub 202 contacts the spring housing 235. More significantly, the outer cannula hub is drawn proximally until the charging ramp 210 engages the ramp 247 of the spring housing, as shown in FIG. 19*b*. In this position, the outer cannula spring 270 is fully charged and the outer cannula 204 is in position to obtain an additional tissue sample. It can be appreciated that the inner cannula 220 is at its farthest proximal (left side) extent while the outer needle 204 is being retracted. In this position, the outer needle can be retracted along with the core tissue sample embedded within the distal end of the outer needle without risk of the distal end of the inner needle contacting the tissue sample. The proximal travel of the inner cannula 220 can thus be calibrated to approximate the distal travel of the outer cannula when obtaining the tissue sample. As an alternative, the plunger 250 and inner cannula hub 216 can be configured for engagement when the inner cannula is in its farthest proximal extent. More particularly, the guide arm 259 and cannula hub 216 can be configured with an interlock that engages as the plunger 250 is moved farther proximally as shown in FIG. 19*b*. This additional movement of the inner cannula 220 will ensure that it does not interfere with the tissue sample embedded within the outer cannula.

Figure 20:
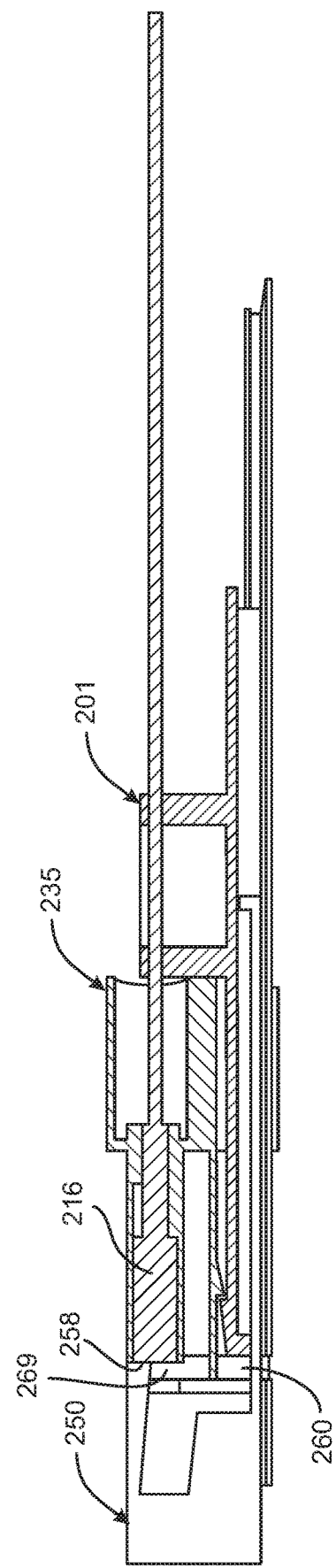
FIG. 20 is a perspective partial cross-sectional view of the charging and firing mechanism of FIG. 8 shown as the plunger is advanced.

As is evident in FIG. 19*b*, the inner cannula 220 is not yet in its charged position. Once the biopsy device has been removed from the tissue site, it is necessary to expel the core sample. Thus, the plunger 250 is depressed distally, i.e., to the right in FIG. 20, until the inner cannula stop 258 contacts the proximal face 216*a* of the inner cannula hub 216. Continued movement of the plunger compresses the spring 272 within the proximal spring casing 242. Moreover, continued movement of the plunger drives the inner cannula distally toward the distal end of the outer cannula, thereby pushing the core tissue sample out of the outer cannula. The mechanism 200 is then in its charged condition of FIG. 8 so that the device is ready to obtain another core tissue sample. A latch mechanism may be provided between the plunger 250 and the spring housing 235, tracking guide 225 or device housing to hold the plunger against the force of the inner cannula spring 272 until the latch is disengaged to retract the outer cannula in the steps shown in FIGS. 19*a*, 19*b*.

The present disclosure should be considered as illustrative and not restrictive in character. It is understood that only certain embodiments have been presented and that all changes, modifications and further applications that come within the spirit of the disclosure are desired to be protected.

What is claimed is:

1. A biopsy device comprising:
    an outer cannula hub;
    an elongated outer cannula carried at a proximal end by said outer cannula hub and defining a tissue cutting edge at an opposite distal end;
    an inner cannula hub;
    an elongated inner cannula carried at a proximal end by said inner cannula hub and concentrically slidably disposed within said outer cannula;
    a housing defining a first cavity, a second cavity, and a spring hub between said first and second cavities, said spring hub defining a bore in communication between said first cavity and said second cavity, the housing configured to support at least a portion of the inner cannula hub in the first cavity, the bore configured for passage of said inner cannula therethrough;
    an outer cannula spring disposed within said first cavity in contact between said spring hub and said outer cannula hub, said outer cannula spring having a compressed state in which the spring produces a force directed distally against said outer cannula hub;
    an inner cannula spring disposed within said second cavity in contact between said spring hub and said inner cannula hub, said inner cannula spring having a compressed state in which the inner cannula spring produces a force directed proximally against said inner cannula hub;
a latch arrangement configured to hold said outer cannula hub in a charged position compressing said outer cannula spring within said first cavity;
a stop arrangement configured to hold said inner cannula hub in a charged position compressing said inner cannula spring within said second cavity; and
a trigger configured to sequentially release said latch arrangement to disengage said outer cannula hub from said charged position to allow the outer cannula spring to drive said outer cannula distally into a tissue site and release said stop arrangement to disengage said inner cannula hub from said charged position to allow the inner cannula spring to drive said inner cannula proximally.

2. The biopsy device of claim 1, wherein:
the latch arrangement includes:
a latch element associated with the outer cannula hub; and
a flex arm associated with said housing and defining a stop face for engaging the latch element, the flex arm configured to be resiliently displaced;
said latch element and stop face arranged to hold said outer cannula hub adjacent the first cavity in the charged position; and
said trigger includes a release element arranged to be pressed against said flex arm to disengage said stop face from said latch element.

3. The biopsy device of claim 2, wherein:
said stop arrangement includes a resilient arm defining a second stop face aligned with said inner cannula hub when the inner cannula hub is in said charged position; and
said trigger includes a beam arranged to be pressed against said resilient arm to disengage said second stop face from said inner cannula hub.

4. The biopsy device of claim 3, wherein said release element is integral with said beam and said beam is arranged within the biopsy device for movement perpendicular to the concentric outer and inner cannulae.

5. The biopsy device of claim 4, wherein said trigger is configured so that said release element contacts the flex arm before the beam contacts said resilient arm.

6. The biopsy device of claim 3, wherein said release element is integral with said beam and said beam is arranged within the biopsy device for movement parallel to the concentric outer and inner cannulae.

7. The biopsy device of claim 1, wherein:
said stop arrangement includes a resilient arm defining a second stop face aligned with said inner cannula hub when the inner cannula hub is in said charged position; and
said trigger includes a beam arranged to be pressed against said resilient arm to disengage said second stop face from said inner cannula hub.

8. The biopsy device of claim 1, wherein the inner surface of said outer cannula defines an angled countersink at the distal end terminating in said tissue cutting edge.

9. The biopsy device of claim 8, wherein the tissue cutting edge includes a Franseen tip.

* * * * *